United States Patent [19]

Totakura

[11] Patent Number: 5,383,903
[45] Date of Patent: Jan. 24, 1995

[54] DIMETHYLSILOXANE-ALKYLENE OXIDE COPOLYMER COATINGS FOR FILAMENTS

[75] Inventor: Nagabhushanam Totakura, Norwalk, Conn.

[73] Assignee: United States Surgical Corporation, Norwalk, Conn.

[21] Appl. No.: 932,961

[22] Filed: Aug. 20, 1992

[51] Int. Cl.6 .................... A61L 17/00; A61B 17/04
[52] U.S. Cl. ........................... 606/228; 606/231; 604/265
[58] Field of Search ............. 606/228, 229, 230, 231; 604/265; 524/262, 265

[56] References Cited

U.S. PATENT DOCUMENTS

| 3,187,752 | 4/1962 | Glick . |
| 3,280,160 | 10/1966 | Bailey . |
| 3,418,354 | 12/1968 | Wheeler . |
| 3,541,127 | 11/1970 | Hughes et al. . |
| 3,629,310 | 12/1971 | Bailey . |
| 3,755,399 | 8/1973 | Nitzsche et al. . |
| 3,837,891 | 9/1974 | Tietz . |
| 3,839,743 | 10/1974 | Schwarcz ........................ 623/11 |
| 4,043,344 | 8/1977 | Landi et al. . |
| 4,184,004 | 1/1980 | Pines et al. . |
| 4,207,071 | 6/1980 | Lipowitz et al. . |
| 4,217,228 | 8/1980 | Koerner et al. . |
| 4,283,519 | 8/1981 | Pines et al. . |
| 4,359,545 | 11/1982 | Ona et al. . |
| 4,578,116 | 3/1986 | Rott et al. . |
| 4,590,224 | 5/1986 | Frisch ........................... 521/155 |
| 4,617,340 | 10/1986 | Tanaka et al. . |
| 4,624,676 | 11/1986 | White et al. . |
| 4,649,920 | 3/1987 | Rhum ........................ 606/231 X |
| 4,699,967 | 10/1987 | Eichenauer et al. . |
| 4,711,241 | 12/1987 | Lehmann .................. 606/231 X |
| 4,738,950 | 4/1988 | Vanier et al. ................. 503/227 |
| 4,774,937 | 10/1988 | Scholz et al. ..................... 602/8 |
| 4,784,665 | 11/1988 | Ona et al. . |
| 4,937,277 | 6/1990 | O'Lenick, Jr. . |
| 4,983,180 | 1/1991 | Kawai et al. ................. 606/230 |
| 5,102,420 | 4/1992 | Hunter et al. ................ 606/231 |
| 5,102,707 | 4/1992 | Canivene et al. .............. 428/44 |
| 5,123,912 | 6/1992 | Kaplan et al. ................ 606/230 |
| 5,147,383 | 9/1992 | Bezwada et al. .............. 606/231 |
| 5,194,473 | 3/1993 | Shinoda et al. ............... 524/263 |
| 5,244,967 | 9/1993 | Inoue et al. .................. 524/588 |
| 5,294,649 | 3/1994 | Gerber ......................... 523/145 |

FOREIGN PATENT DOCUMENTS

| 0241599 | 11/1962 | Australia ...................... 606/231 |
| 0677420 | 1/1964 | Canada ......................... 606/231 |
| 0258749 | 3/1988 | European Pat. Off. . |
| 0331774 | 9/1989 | European Pat. Off. . |
| 0486305 | 5/1992 | European Pat. Off. . |
| 1815899 | 7/1969 | Germany ...................... 606/231 |
| 2063099 | 7/1971 | Germany ...................... 606/231 |
| 0031761 | 2/1985 | Japan .......................... 606/231 |
| 0040560 | 2/1988 | Japan .......................... 606/231 |
| 1164339 | 6/1985 | U.S.S.R. ..................... 606/231 |
| WO8903851 | 5/1989 | WIPO . |

OTHER PUBLICATIONS

Silicon Compounds: Register and Review; Petrarch Systems Product Literature, 1987.
Silicon Compounds: Register and Review; Huls American Inc. Product Literature, 1991.

Primary Examiner—C. Fred Rosenbaum
Assistant Examiner—V. Alexander

[57] ABSTRACT

Filaments or sutures are coated with a dimethylsiloxane-alkylene oxide copolymer to improve the handling characteristics of the filament or suture.

11 Claims, No Drawings

DIMETHYLSILOXANE-ALKYLENE OXIDE COPOLYMER COATINGS FOR FILAMENTS

FIELD OF THE INVENTION

The present invention relates generally to coatings for filaments. More particularly, the present invention relates to dimethylsiloxane-alkylene oxide copolymer coatings for filaments or sutures.

BACKGROUND OF THE INVENTION

Many synthetic materials are presently used as surgical sutures. These materials may be used as single filament strands, i.e., monofilament sutures, or as multifilament strands in a braided, twisted or other multifilament construction. Synthetic sutures have been made from materials such as polypropylene, nylon, polyamide, polyethylene, polyesters such as polyethylene terephthalate, and segmented polyether-ester block copolymers. In addition, absorbable synthetic sutures have been prepared from synthetic polymers such as polymers containing glycolide, lactide, dioxanone and/or trimethylene carbonate.

Natural materials have also been used to make sutures. For example, silk has been used to make non-absorbable sutures. As another example, catgut sutures are absorbable sutures made from a natural material.

Sutures intended for the repair of body tissues must meet certain requirements: they must be non-toxic, capable of being readily sterilized, they must have good tensile strength and have acceptable knot-tying and knot characteristics.

The performance of a suture in terms of knot run down, knot security and tissue drag are particularly important to surgeons. Knot run down performance, which reflects the ease of placement of a knot tied in a suture, is important in surgical procedures where it is necessary that a knot be tied in a suture when the knot is deep inside a surgical or natural opening. For instance, a dental surgeon may need to tie a knot inside a patient's mouth. An intravaginal hysterectomy requires suturing in restricted quarters. One technique frequently used is to tie a square knot that can be run down from an exterior location where the knot is first tied to lie against tissue with a desired degree of tightness. The knot is snugged down so that it is holding with a degree of firmness chosen by the surgeon for a particular situation and then additional throws are tied down against the first throws of the square knot. In some instances, the first throw is a double twist followed by a single throw to form a surgeons' knot, with additional throws to form additional square knots on top as needed. The ease with which a knot runs down the suture depends on a number of factors such as composition of the suture, braid structure of the suture, and the nature of the coating, if any, applied to the suture. Preferably, the knot runs down the suture smoothly and easily.

Knot security is the ability of the knot to hold without slipping for an acceptable length of time. The characteristics of the suture material which allow a knot to hold securely are somewhat at odds with the characteristics of the suture material which provide satisfactory knot run down performance, since knot security requires that the suture grab itself while knot run down requires that the suture pass smoothly over itself. Accordingly, a balance of these two characteristics is normally required.

It is also desirable for a suture to have low tissue drag, which is a measure of the force required to pull a suture through tissue. High drag forces results in chatter as the suture passes through tissue, makes it more difficult for the surgeon to align tissue neatly, and increases the time to complete the closure being made with the suture.

A wide variety of coatings have been applied to sutures of various types to improve one or more characteristics of the suture. See, for example, U.S. Pat. Nos. 3,187,752; 3,527,650; 3,942,523; 4,105,304; and 4,185,637.

U.S. Pat. No. 3,187,752 describes non-absorbable silicone coated sutures, but does not describe the copolymers employed in the present invention or the superior results which are achieved by using those copolymers.

Fibers or textile treatments which include organo silicon compounds have been described in, inter alia, U.S. Pat. Nos. 3,280,160; 3,418,354; 4,283,519; 4,359,545; 4,217,228; 4,784,665; 3,837,891; 4,207,071; 4,184,004; 4,578,116; 4,937,277; 4,617,340; and 4,624,676.

Siloxane-oxyalkylene copolymers have been described in U.S. Pat. Nos. 3,629,310; 3,755,399; 3,280,160; 3,541,127; and 4,699,967. U.S. Pat. No. 4,043,344 describes non-absorbable sutures coated with polyoxyethylene-polyoxypropylene copolymer lubricant.

SUMMARY OF THE INVENTION

It has now been found that a suture formed from one or more filaments and coated with a dimethylsiloxane-alkylene oxide copolymer exhibits a good balance of knot run down and knot security characteristics, and superior tissue drag characteristics.

In another aspect, the present invention embraces a method for improving the handling characteristics of a suture by applying to the suture a coating comprising a dimethylsiloxane-alkylene oxide copolymer.

Preferred coatings comprise a copolymer including blocks which contain dimethylsiloxane and blocks which contain polyethylene oxide, polypropylene oxide or combinations thereof.

DESCRIPTION OF PREFERRED EMBODIMENTS

Sutures in accordance with the present invention are prepared by applying a coating to one or more filaments. Preferably, the suture is made from a synthetic material. Suitable synthetic materials include, but are not limited to polypropylene, nylon, polyamide, polyethylene, polyesters such as polyethylene terephthalate, segmented polyether-ester block copolymers and polyurethanes. When more than one filament is used, the filaments may be braided, twisted, entangled, intertwined or arranged in some other multifilament configuration. A particularly useful braid structure for sutures is the spiroid braid structure described in U.S. Pat. Nos. 5,019,093 and 5,059,213 the disclosures of which are incorporated herein by reference.

The coating applied to the monofilament or multifilament structure comprises a dimethylsiloxane-alkylene oxide copolymer. Suitable copolymers include those having blocks comprising dimethylsiloxane and blocks comprising polyethylene oxide, polypropylene oxide or combinations thereof. Preferred copolymer coatings contain alkylene oxide in an amount less than about 75 percent by weight of the polymer. Such copolymers are commercially available from Hüls America, Inc., Piscataway, N.J. Preferably, the copolymer used for the coating will have a relatively low water solubility. The copolymer identified by Hülls America, Inc. as 072 is a particularly preferred coating material.

Preferred coating material for use in the present invention have the following composition:

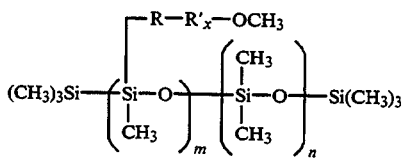

wherein R represents a divalent hydrocarbon group such as an alkyl or alkylene group and R' represents an alkylene oxide group or combination of different alkylene oxide groups and m, n and x represent number of repeating units.

The copolymer coating is applied to the monofilament or multifilament in an amount of between about 0.01 to 20 percent by weight based upon the weight of the filament or filaments to which the coating is applied. Preferably, the coating is applied in an amount of from about 0.1 to 10 weight percent. Most preferably, the amount of coating is between about 0.5 and 5 weight percent. The amount of coating applied to the suture may be adequate to coat all surfaces of the suture. Preferably, the amount of coating applied will be that amount sufficient to improve the handling characteristics of the suture, regardless of whether the entire surface of the suture is coated. The term coating as used herein is intended to embrace both full and partial coatings.

The coating may be applied by any conventional method. For example, the coating material may be melted and applied to filaments as a melt, provided that the melting temperature of the filaments is sufficiently greater than the melting temperature of the coating material to avoid significant degradation of the filaments. As another example, the coating material may be dissolved in an appropriate solvent, applied to filaments as a solution and then the solvent evaporated to leave a copolymer coating. An appropriate solvent will dissolve the coating material, but have no significant detrimental effect on the integrity of the filaments during the coating process.

The coatings may optionally contain other materials including colorants, such as pigments or dyes, fillers or therapeutic agents, such as antibiotics, growth factors, etc. Depending on the amount of coating present, these optional ingredients may constitute up to about 25 percent by weight of the coating.

The examples below are illustrative of sutures in accordance with the present invention.

EXAMPLE

A 5% solution of PS072 in methylene chloride solvent was prepared by mixing 5 grams of the copolymer in 100 ml of methylene chloride at room temperature. Multifilament dacron spiroid braids of the structure described in U.S. Pat. No. 5,059,213 were prepared on a 20 carrier braider. The braids had a denier of about 828, corresponding to a size 2/0 suture. The coating solution was applied to the braid and the solvent evaporated off to produce coatings of 1.5% based on the weight of the braid. For comparison purposes, an identical, uncoated Dacron braid and an identical Dacron braid coated with a conventional silicone coating were also prepared. The results of knot run down, knot security and knot pull tests on the suture of this invention, an uncoated control suture (Control A) and a control suture coated with a silicone presently used on Dacron sutures (Control B) are presented in Table I. The silicone coating used on Control B was a 1.5% coating of MDX-4-4159 (available from Dow-Corning Inc.) which is a curable solution of an amino functional dimethylsiloxane.

TABLE I

| Suture | Suture Size | % Coating | Suture Drag (gms)** | Knot Pull Strength (kg) | Knot Security* |
|---|---|---|---|---|---|
| Example 1 | 2/0 | 1.5 | 22.5 | 2.62 | 0/10 |
| Control A | 2/0 | 0 | 187 | 2.36 | 0/10 |
| Control B | 2/0 | 1.5 | 170 | 2.49 | 0/10 |

*Number of knot failures out of 10 samples.
**Average of two tests.

Suture tissue drag data was generated using a tester manufactured by Instron Corporation (Model 4301) as follows: Each armed suture strand is passed through the drag medium in a "W" pattern ensuring that approximately one inch spacing is maintained between entry and exit sites of the suture. The suture is then threaded under the lower Instron pulley and attached to needle holders. The needle holders are then secured to the Instron load cell and the suture is withdrawn from the drag medium at a constant rate of 300 mm/min. The magnitude of the force required to withdraw the suture is recorded. Large variations in force over small periods of time during withdrawal of the suture is identified as "chatter".

The procedure for measuring knot security was as follows:

A 2 cm loop was tied with a surgeon's square knot (1-1-1-1) securing the throws at 20% of the USP XXII knot strength for 2/0 nonabsorbable sutures (n—10 loops per group). The loop was placed next to a cloth-wrapped mandrel rotating at 0.5 rpm. The fixtures were secured to allow contact of the cloth material against the fourth, i.e. top throw of each knot. The cloth wrapping was moistened with 37° C. water prior to the test and was periodically remoistened during the test. Each pass of the cloth across the knot (for a total of 100 passes), the knot was inspected for top throw security. For a knot to be considered secure, the 3 mm ears must not have come undone and there must have been no relaxation of the knot or loss of the fourth throw.

Knot pull tensile strength was tested in accordance with U.S.P. XXI, tensile strength, sutures (881).

On both the coated suture of the present invention and the controls, the ability of a knot to run down the suture was acceptable, with none of ten test knots made with each suture snagging while being slid down the suture.

As is evidenced from the data in Table I, the coated suture of the present invention demonstrated improved knot pull strength and tissue drag while maintaining acceptable knot security.

We claim:

1. A surgical suture comprising:
   a filament of a synthetic material;
   a coating on said filament, said coating comprising a dimethylsiloxane-alkylene oxide copolymer.

2. A suture as in claim 1 wherein said copolymer comprises a block containing dimethylsiloxane and a block containing polyethylene oxide, polypropylene oxide or a combination thereof.

3. A suture as in claim 1 wherein said synthetic material is selected from the group consisting of propylene, nylon, polyamide, polyesters, segmented polyetherester block copolymers and polyurethanes.

4. A suture as in claim 1 wherein said synthetic material is polyethylene terephthalate.

5. A suture as in claim 1 wherein the suture comprises a plurality of filaments.

6. A suture as in claim 1 wherein said filaments are braided.

7. A suture as in claim 1 wherein said sutures are braided to form a spiroid braid.

8. A suture as in claim 1 wherein said coating comprises a copolymer of the following formula:

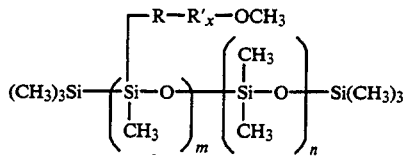

wherein R represents a divalent hydrocarbon group such as an alkyl or alkylene group and R' represents an alkylene oxide group or combination of different alkylene oxide groups and m, n and x represent number of repeating units.

9. A suture as in claim 8 wherein said R' group is selected from the group consisting of ethylene oxide, propylene oxide and combinations thereof.

10. A method of closing a wound in tissue comprising:
providing a suture comprising one or more filaments having thereon a coating, said coating comprising a dimethylsiloxane-polyalkylene oxide copolymer; and
approximating and securing the tissue with said suture.

11. A method as in claim 10 wherein said copolymer comprises a block containing dimethylsiloxane and a block containing polyethylene oxide, polypropylene oxide or a combination thereof.

* * * * *